(12) United States Patent
Weber et al.

(10) Patent No.: US 7,192,744 B2
(45) Date of Patent: Mar. 20, 2007

(54) TARGETED TRANSFECTION OF CELLS USING A BIOTINYLATED DENDRIMER

(75) Inventors: Martin Weber, Leichlingen (DE); Jörg Dennig, Hilden (DE); Christoph Erbacher, Haan (DE)

(73) Assignee: Qiagen GmbH, Hilden (DE)

( * ) Notice: Subject to any disclaimer, the term of this patent is extended or adjusted under 35 U.S.C. 154(b) by 371 days.

(21) Appl. No.: 10/240,981

(22) PCT Filed: Apr. 3, 2001

(86) PCT No.: PCT/EP01/03746

§ 371 (c)(1),
(2), (4) Date: Oct. 4, 2002

(87) PCT Pub. No.: WO01/76633

PCT Pub. Date: Oct. 18, 2001

(65) Prior Publication Data

US 2003/0096280 A1    May 22, 2003

(51) Int. Cl.
C12P 19/34 (2006.01)
C12N 15/00 (2006.01)
C12N 15/10 (2006.01)
C12N 15/11 (2006.01)

(52) U.S. Cl. .................. 435/91.1; 435/455; 536/23.1

(58) Field of Classification Search ............... 536/23.1; 514/44
See application file for complete search history.

(56) References Cited

U.S. PATENT DOCUMENTS

| 4,507,466 A | 3/1985 | Tomalia et al. ............. 528/332 |
| 4,558,120 A | 12/1985 | Tomalia et al. ............. 528/363 |
| 4,568,737 A | 2/1986 | Tomalia et al. ............. 528/332 |
| 4,587,329 A | 5/1986 | Tomalia et al. ............. 528/363 |
| 4,631,337 A | 12/1986 | Tomalia et al. ............. 528/391 |
| 4,694,064 A | 9/1987 | Tomalia et al. ............. 528/332 |
| 4,713,975 A | 12/1987 | Tomalia et al. ............. 73/865.8 |
| 4,737,550 A | 4/1988 | Tomalia et al. ............. 525/418 |
| 4,857,599 A | 8/1989 | Tomalia et al. ............. 525/259 |
| 4,871,779 A | 10/1989 | Killat et al. ................. 521/28 |
| 5,714,166 A * | 2/1998 | Tomalia et al. ............. 424/486 |

FOREIGN PATENT DOCUMENTS

| EP | 0 274 180 | 11/1993 |
| EP | 0 234 408 | 3/1995 |
| EP | 0 247 629 | 10/1995 |
| WO | WO 84/02705 | 7/1984 |
| WO | WO 93/19768 | 10/1993 |
| WO | WO 95/02397 | 1/1995 |

OTHER PUBLICATIONS

Molecular Biology Reagents/Protocols 1992, United States Biochemical Corporation, 1991, Cleveland, Ohio, pp. 218-219.*
Schoeman et al., *J. Drug Target*, 2: 509-516 (1995).
Tang et al., *Biconjug. Chemistry*, 7: 703-714 (1996).
Tomalia et al., *Angew Chem. Int. Ed.*, 29: 138 (1990).
Wilbur et al., *Bioconjug. Chem.*, 9: 813-825 (1998).

* cited by examiner

*Primary Examiner*—James Martinell
(74) *Attorney, Agent, or Firm*—Yankwich & Associates, P.C.; Leon R. Yankwich; Michael R. Wesolowski

(57) ABSTRACT

The present invention relates to processes for the targeted transfection of cells, compositions which may be used for such processes, and corresponding pharmaceutical compositions for gene therapy. In particular, the invention relates to a process for introducing nucleic acid into cells comprising the steps of (a) mixing a nucleic acid with a dendrimer, in which a proportion of the dendrimer molecules are biotinylated; (b) mixing the resulting complex of nucleic acid and dendrimer with a second complex consisting of avidin or streptavidin and a biotinylated target-specific binding molecule; and (c) incubating the complex formed in step (b) with cells. Dendrimers which are well suited to the present invention include, for example, partially solvolysed polyamidoamine (PAMAM) dendrimers. Target-specific binding molecules are, in particular, cell-type-specific markers of the cell surface of the target cells.

25 Claims, 11 Drawing Sheets

TARGETED TRANSFECTION OF CELLS USING A BIOTINYLATED DENDRIMER

This application is the United States national filing under 35 U.S.C. §371 of international (PCT) application No. PCT/EP01/03746, filed Apr. 3, 2001, claiming priority to German application 10016881.7, filed Apr. 5, 2000.

The present invention relates to processes for the targeted transfection of cells and compositions which may be used for such processes.

Various methods of introducing genetic material into cells are known from the prior art. For transfection in vivo, essentially two methods are used, virus-mediated gene transfer and transfection using cationic liposomes. The viral vectors used are adenoviruses and retroviruses, which are capable of transfecting nonviral DNA into mitotically active cells. The cationic liposomes interact with the negatively charged phosphate backbone of the DNA. The resulting complex is added to the cells and endocytosed by the cells. For transfection in vitro additional methods are available, such as calcium phosphate precipitation, DEAE (diethylaminoethyl) dextran transfection and electroporation. In the calcium phosphate method, DNA is mixed with $CaCl_2$ in a phosphate buffer. The calcium phosphate complex formed binds to the cell membrane and is endocytosed. The positively charged DEAE-dextran interacts with the negatively charged phosphate backbone of the DNA. The DEAE-dextran-DNA complex binds to the cell surface and is endocytosed. In electroporation, cells are mixed with DNA. For a brief moment a high voltage is applied. Pores are produced in the cell membrane through which the DNA is taken up.

The methods mentioned above have various disadvantages. Thus, viral vectors do admittedly allow efficient transfection of cells in vivo. However, their biological risk potential is very high. The efficiency when using cationic liposomes in vivo is very low. Moreover, neither of the in vivo processes allows targeted transfection of individual cell types in the tissue. In the in vitro applications there is the particular problem that suspended cell lines (particularly T and B cell lines) are extremely difficult to transfect using the chemical transfection reagents and methods. Unlike adherent cells, in which efficiencies of more than 50% transfected cells can often be achieved, the efficiencies with suspended cells are generally 0% to 5% transfected cells. In electroporation the transfection efficiencies in suspended cells are generally quite low. However, this method often provides the possibility of transfecting cell lines which cannot be transfected at all by other methods. In this method, however, the transfection kills 50% to 70% of the cells. Also the quantity of DNA and cells per batch required for this transfection method is significantly higher than for other methods. Retroviral vectors do admittedly enable suspended cells to be transfected efficiently. However, the method is very complicated and expensive. In particular, retroviral vectors have a high biological risk potential.

Dendrimers are three-dimensional polymers which are made up of reiterative sequences around a nucleus and can be produced in various molecular weights and sizes (Tomalia et al., Angew Chem Int Ed 1990, 29:138). The complexing of dendrimers with nucleic acids and the use of dendrimers for transfecting cells are known from WO 95/02397. Tang et al., Bioconjugate Chem 1996, 7: 703–714 describe the activation of polyamidoamine dendrimers by thermal degradation in order to improve transfection efficiency. The use of dendrimers on their own as transfection reagents, however, is also fraught with the disadvantages described above.

Schoeman et al., J Drug Target 1995, 2(6):509–516 describe a system for the targeted transfer of DNA into cells in which biotinylated polylysine is used which is bound to biotinylated transferrin via streptavidin.

Wilbur et al., Bioconjug Chem 1998, 9(6):813–825 describe biodistribution experiments with biotinylated starburst dendrimers.

The objective of the present invention was to provide improved transfection methods and the means required therefor, which make it possible in particular to incorporate nucleic acids even into cells which are difficult to transfect, such as suspended cells.

This objective is achieved by means of a process for introducing nucleic acid into cells, comprising the steps of
(a) mixing a nucleic acid with a dendrimer, in which a proportion of the dendrimer molecules are biotinylated;
(b) mixing the resulting complex of nucleic acid and dendrimer with a second complex consisting of avidin or streptavidin and a biotinylated target-specific binding molecule;
(c) incubating the complex formed in step (b) with cells.

The nucleic acid, which is synonymous here with the term polynucleotide, may be a ribonucleic acid (RNA), deoxyribonucleic acid (DNA) or a mixed form. Generally, it may be any type of polynucleotide which is an N-glycoside or C-glycoside of a purine or pyrimidine base or of a modified purine or pyrimidine base, i.e. it may also contain bases which do not occur in nature. Apart from the base itself, the sugar group may also be modified. Nucleic acids with modified linking of the subunits, such as phosphorothioate or amidate bonds, are included. The nucleic acid may be single-, double- or multi-stranded, linear or circular. It may correspond to a molecule occurring in a cell such as genomic DNA or messenger RNA (mRNA) or it may be produced in vitro such as complementary DNA (cDNA), antisense RNA (aRNA), or synthetic nucleic acids. The nucleic acid may consist of a few subunits, at least two subunits, preferably eight or more subunits such as oligonucleotides, several hundred subunits up to several thousand subunits, such as certain expression vectors. Preferably, the nucleic acid contains the coding information for a polypeptide in functional connection with regulatory sequences which allow expression of the polypeptide in the cell into which the nucleic acid is introduced. Thus, in a preferred embodiment, the nucleic acid is an expression vector. In another embodiment it is an antisense oligonucleotide which is able to suppress the expression of a particular gene, for example, by hybridising with another nucleic acid in the cell into which this antisense oligonucleotide is introduced.

A dendrimer for the purposes of the present invention is a branched polymer which is a three-dimensional highly ordered compound, in which branched oligomeric/polymeric sequences may be formed around a nuclear molecule by reiterative reaction sequences, and which under certain conditions has a positively charged outer surface as a result of suitable functional terminal end groups (polycationic dendrimer). Dendrimers of this kind and their preparation are described in WO 84/02705, U.S. Pat. Nos. 4,507,466, 4,558,120, 4,568,737, 4,587,329, 4,631,337, 4,694,064, 4,713,975, 4,737,550, 4,871,779, 4,857,599, EP 0 234 408, EP 0 247 629, EP 0 271 180, and especially Tange et al., supra, WO 95/02397, and Tomalia et al., supra.

Suitable nuclear molecules have at least two reactive groups by means of which the oligomeric/polymeric sequences may be linked to the nucleus, or they are suitable for introducing reactive groups of this kind. Examples of such reactive groups are hydroxyl, ether, amino, imino, amido, imido, ammonium, halogen, carboxyl, carboxyhalide, mercapto groups, etc. Preferred nuclear molecules are ammonia, tris-(2-aminoethyl)amine (TAEA), lysine, ornithine, pentaerythritol and ethylenediamine (EDA).

The branched oligomeric/polymeric sequences may be synthesised around these nuclear molecules by the stepwise addition of monomers. Each reaction cycle that produces new branching points thereby generates a higher "generation" of the dendrimer. Pharmaceutically well tolerated sequences such as polyamidoamines, for example, which may be prepared by reacting an alkyl ester of an α,β-ethylenically unsaturated carboxylic acid or an α,β-ethylenically unsaturated amide with an alkylene-polyamine or a polyalkylene-polyamine, are preferred.

The terminal groups of the oligomeric/polymeric sequences, which form the outer surface of the dendrimer, are supposed to have the ability to acquire positive charges under suitable conditions, for example in aqueous solution at physiological pH values. Examples of such groups are primary, secondary, tertiary and quaternary aliphatic or aromatic amines, guanidinium groups or azoles, which may also be substituted with S or O, or combinations thereof. The terminal cationic groups may be present in an amount of 10 to 100% of all terminal groups, preferably 50% to 100%. The dendrimer may also comprise non-cationic terminal groups in an amount of from 0 to 90%, e.g. hydroxyl, cyano, carboxyl, mercapto, amide or thioether groups.

Dendrimers which are suitable for the present invention include, for example, polyamidoamine (PAMAM) dendrimers which may be synthesised around ammonia, tris-(2-aminoethyl)amine (TAEA) or ethylenediamine (EDA) as nuclear molecules by stepwise addition of the two monomers methacrylate and ethylenediamine (Tang et al., supra). The terminal groups of such a dendrimer are preferably primary amino groups. 5th, 6th or 7th generation PAMAM dendrimers are preferred, particularly 6th generation, according to Tang et al., supra. The theoretical molecular weights, number of terminal amines and hydrodynamic radii of such PAMAM dendrimers may be found in the publication of Tang et al., supra.

The dendrimers are preferably not entirely intact or highly symmetrical molecules according to their ideal structure, but have, to some extent, structural defects, faults or deviations from the ideal structure. It has been found that structural defects of this kind may increase the usefulness of dendrimers as transfection reagents (Tang et al., supra). Such defects may be produced, for example, by partial solvolytic degradation of the dendrimer. Suitable solvents for this include, for example, water, 1-butanol, 2-butanol or 2-ethoxyethanol. The solvolysis may be accelerated by heat. Thus, for example, boiling in water for 5 to 15 hours, preferably 7 to 12 hours, in a 6th generation TAEA-PAMAM dendrimer (6-TAEA-PAMAM) leads to a significant increase in the transfection efficiency. For a 5-TAEA-PAMAM the preferred range is 5 to 12 hours, for a 6-EDA-PAMAM it is 10 to 15 hours. The optimum reflux times in other solvents may vary accordingly, e.g. 20 to 60 hours, preferably 30 to 50 hours, most preferably 40–50 hours in anhydrous 1-butanol for 6-TAEA-PAMAM. As an alternative to solvolytic degradation the abovementioned structural defects may also be produced during the actual synthesis, for example by the batchwise addition of monomers in each cycle which cannot generate any branching point or allow any chain lengthening, e.g. N,N'-dimethylacrylamide. Dendrimers with structural defects, faults or deviations from the ideal structure as described above, particularly those which may be produced by partial solvolysis, should be referred to here as activated dendrimers. It is assumed that the improved usefulness of activated dendrimers as transfection reagents is connected to their greater steric flexibility.

An activated dendrimer which is highly suitable for the present invention is contained in the product SuperFect® made by Messrs Qiagen GmbH, Hilden, Germany.

The proportion of biotinylated dendrimer molecules in the total quantity of dendrimer molecules in the complex may be from 0.01 to 100% (mol/mol), preferably 0.5 to 50% (mol/mol), more preferably 5 to 20% (mol/mol), most preferably 10 to 15% (mol/mol). Advantageously, a pre-prepared mixture of biotinylated and non-biotinylated dendrimer may be reacted with the nucleic acid in order to form the complex according to the invention, but the three components may also be mixed together in a different order or simultaneously. A mixture of biotinylated and non-biotinylated dendrimer may be prepared by mixing biotinylated and non-biotinylated dendrimer in ratios by mass of 1:1 to 1:256, preferably 1:2 to 1:128, more preferably 1:4 to 1:24, most preferably 1:6 to 1:10. The mixing may expediently be done by mixing together aqueous solutions of the components.

By biotinylated dendrimer is meant here a dendrimer composition in which at least 80%, preferably at least 90%, more preferably at least 95% and most preferably at least 98% or 99% of the dendrimer molecules are linked to one or more biotin molecules.

Biotin (Merck Index No. 1272, 12th Ed., Merck & Co., Whitehouse Station, N.J., USA) and methods of biotinylation, i.e. for linking biotin or biotin derivatives to other substances, normally using an activated biotin or biotin derivative, are known from the prior art (Bayer et al., Anal Biochemistry 1985, 149:529–536; Bengtstrom et al., Nucleosides and Nucleotides 1990, 9: 123; Pantano and Kuhr, Anal Chem 1993, 65: 623–630; Bayer and Wilchek, Method of Biochemical Analysis 1980, 26: 1–45; Hofmann et al., Avidin binding of carboxyl-substituted biotin and analogues, Biochemistry 1982, 21: 978–984; Leary et al., Proc Natl Acad Sci USA 1983, 80: 4045–4049; Costello et al., Clin Chem 1979, 25: 1572–1580; Spiegel and Wilchek, J Immunol 1981, 127: 572–575; Rosenberg et al., J Neurochem 1986, 46: 641–648).

By activated biotin or activated biotin derivatives are meant here compounds which are derived from biotin and which are suitable for biotinylation reactions by the insertion of a reactive group, particularly a leaving group, at a carboxyl function of the side chain of the biotin. The term "biotin derivative" includes in particular modified forms of biotin in which, for example, the side chain of the biotin has been lengthened, so as to producer a spacer function. Other functional groups which allow covalent bonding of the biotin to dendrimers, proteins or other substances may also be introduced. An example of such a derivative is 6-(biotinamido)hexanoic acid (biotinamidocaproic acid) and the activated derivatives thereof such as N-hydroxysuccinimide esters of biotinamidocaproic acid.

The degree of biotinylation of the biotinylated dendrimer molecules, i.e. the number of biotin molecules which are connected to a dendrimer molecule, is preferably 1 or more. Biotinylated dendrimer which has been prepared by reacting dendrimer with a one- to 64-fold molar excess of biotin, more preferably with a 2- to 16-fold excess, better still a 2- to 12-fold excess, e.g. a 3- to 5-fold excess, particularly a 4-fold excess of biotin, is preferred. For the biotinylation of dendrimers, standard methods known per se may be used, such as the reaction of dendrimer with N-succinimidyl N(+)-biotinyl-6-aminocaproate, an activated biotin derivative which additionally contains a hexanoic acid structure as spacer (Hermanson G T, Bioconjugate Techniques, Academic Press, London, Great Britain, 1996, pages 575–580).

Suitable mixing ratios for nucleic acid to dendrimer are from 10:1 (wt/wt) to 1:50 (wt/wt), preferably 1:2 to 1:20, for suspended cells preferably from 1:2 to 1:10 (wt/wt), most preferably about 1:3. The skilled man can determine the optimum mixing ratios for the particular transfection problem by routine experiments.

The nucleic acid and dendrimer are mixed together under conditions in which a complex is formed between the nucleic acid and dendrimer. The skilled man will be familiar with such conditions. Appropriately, this mixing may be done by combining aqueous solutions of the components, in which one or both of these solutions may also be buffered and may optionally contain further additives.

By mixing the nucleic acid and the partially biotinylated dendrimer together (i.e. a mixture of biotinylated dendrimer and non-biotinylated dendrimer in the ratios stated above, for example) under suitable conditions, a complex is formed in which the components are associated with one another by non-covalent interactions.

In a complex of this kind, dendrimer and nucleic acid may also be linked together by covalent bonds.

According to the invention, the complex of nucleic acid and partially biotinylated dendrimer thus obtained may be mixed, under suitable conditions, with a second complex consisting of avidin or streptavidin and a biotinylated target-specific binding molecule and in this way a larger complex may be produced in which the nucleic acid/dendrimer adduct is linked to a target-specific binding molecule via the avidin-biotin system. A complex of this kind allows targeted binding to the surface of cells which carry a binding partner or receptor for the binding molecule, and thereby enables the desired nucleic acid to be introduced target-specifically into such cells. This mixing of the two complexes may expediently be done by combining suitable aqueous solutions of the two complexes, while one or both of these solutions may be buffered and may optionally contain further additives.

Avidin is a glycoprotein known in the art, which is able to bind biotinylated substances with a high affinity (Merck Index No. 920, 12th Ed., Merck & Co., Whitehouse Station, N.J., USA); Fuccillo, Application of the avidin-biotin technique in microbiology, BioTechniques 1985, 3: 494; Methods Enzymol Eds. M. Wilchek, E. A. Bayer 1990, 184: 1–671). It may be obtained from chicken albumin, for example, in which case it has a molecular weight of about 66000 and is commercially obtainable. Alternatively, streptavidin, a protein with a molecular weight of about 60,000 obtained from *Streptomyces avidinii*, may be used (Fuccillo, Application of the avidin-biotin technique in microbiology, BioTechniques 1985, 3: 494; Haeuptle et al., Protein isolated from the bacterium *Streptomyces avidinii*, having a high affinity for biotin, J Bio Chem 1983, 258: 305; Avidin-Biotin technology: Methods Enzymol Eds. M. Wilchek, E. A. Bayer 1990, 184:1–671).

Target-specific binding molecules which bind specifically to particular binding partners are known in large numbers in the prior art. For the purpose of the present invention preferred binding molecules are those which bind to binding partners or receptors exposed on the surface of cells, particularly binding partners or receptors which are specifically expressed by certain cell types. Also preferred are target-specific binding molecules of the kind which are internalised in the interior of the cell, e.g. by receptor-mediated endocytosis, after binding to their binding partner or receptor on the cell surface.

An example of a target-specific binding molecule of this kind is the protein transferrin, the specific binding partner of which, the transferrin receptor, is expressed by a number of cell types, e.g. the B-cell line K562 (AT CC CCL-243). Transferrin is an iron-transporting protein which is actively endocytosed after binding to its receptor. If transferrin is conjugated to a nucleic acid/dendrimer complex via the avidin-biotin system, cells which express the transferrin receptor can be deliberately transfected using such a complex. Another example of a target-specific binding molecule of this kind is an antibody which is specific for the T-cell-specific surface antigen CD3. If an antibody of this kind binds to CD3, the resulting complex is actively internalised into the cell. When a CD3-specific antibody is used as the target-specific binding molecule for the present invention, it is possible to selectively transfect T-cells. A T-cell line which expresses CD3 is the Jurkat cell line (DSMZ ACC 282). Analogously, for the present invention, antibodies may also be used as target-specific binding molecules which are specific for other binding partners or receptors, particularly for cell type-specific cell surface markers which are internalised after binding a ligand. The antibodies used, apart from immunoglobulins which are tetramers or multimers consisting of complete heavy and light chains, may also be antibody derived molecules which are known in the art, e.g. fragments of immunoglobulins which contain the antigen binding domain (e.g. $F_{ab}$ fragments) or recombinant proteins which contain antigen binding domains, particularly the so-called variable regions, of immunoglobulins, optionally in modified form, e.g. humanised antibodies or single-chained antibody molecules (scFv). The expression antibody here is intended to include all such molecules which specifically bind to a binding partner and contain at least one amino acid sequence which is homologous to the variable region of an immunoglobulin chain.

Another example of a target-specific binding molecule is an antibody against CD62E (ELAM-1, E-Selectin), e.g. the monoclonal antibody which is produced by the hybridoma cell line H18/7 (80 CC HB-11684). CD62E is a surface marker for activated vascular epithelial cells which play a central part in inflammatory processes, and a clinical target for gene therapy in this range of indications (Harari et al., Gene Ther 1999, 6(5):801–7).

The target-specific binding molecule may be biotinylated by methods known per se, for example with the N-hydroxysuccinimide ester of biotinamidocaproic acid in aqueous hydrogen carbonate solution (pH 8.5) (Hofmann, K., et al., Avidin binding of carboxyl-substituted biotin and analogues. Biochemistry, 21, 978–984 (1982)). When this biotin derivative is used the caproic acid structure simultaneously introduces a spacer between the binding molecule and the biotin to ensure an optimum interaction between the biotin and avidin or streptavidin. If the target-specific binding molecule is a protein, for example transferrin or an antibody, a biotinylation level of 1 to 15 biotin molecules per binding protein molecule has proved effective, preferably 5 to 13 biotin molecules, more preferably 8 to 12 biotin molecules per protein molecule. The degree of biotinylation may be controlled by the choice of a suitable molar ratio between the reactants in the biotinylation reaction.

The complex of biotinylated target-specific binding protein and avidin or streptavidin may be produced by mixing the two components under suitable conditions. Such conditions are known to anyone skilled in the art. For example, the mixing may be carried out by combining aqueous solutions of the components, whilst one or both of these solutions may be buffered and may optionally contain other additives.

A ratio of nucleic acid/dendrimer complex to avidin or streptavidin of 1:1 to 100:1 (wt/wt) has proved effective, but most preferably 1.5:1 to 4:1 (wt/wt) particularly 2:1 to 4:1. For the ratio of nucleic acids/dendrimer complex to target-specific binding molecule a ratio of 1:1 to 40:1 (wt/wt) has proved effective, particularly 2:1 to 10:1 (wt/wt). Very good results may be obtained for example with ratios of 1:3:2:1 (nucleic acid:dendrimer:avidin:binding protein; wt/wt/wt/wt).

In the process according to the invention it is important to keep to a specific sequence of steps. It has been found that the advantageous effects of the process are particularly brought to bear when both the complex of nucleic acid and dendrimer and the complex of avidin or streptavidin and target-specific binding molecule are pre-prepared before the two complexes are combined.

The resulting complex which functionally combines the components nucleic acid, dendrimer and target-specific binding molecule may be used to introduce the nucleic acid into cells. For this purpose, this complex, hereinafter also referred to as the transfection complex, is incubated with cells, i.e. it is brought into contact with cells under suitable conditions.

Thus, cells or tissue may be incubated in vitro with the transfection complex in a suitable medium. If culture cells are to be transfected, the transfection complex may be added to the culture medium. For transfection in vivo, the transfection complex may be administered to an animal or plant organism, including the human body. It may be administered systemically or topically, and in the case of animals it may be given parenterally in particular, e.g. by intravenous, intraperitoneal, intramuscular, intra- or subcutaneous injection, intravenous infusion, pulmonary, buccal, nasal, dermal or transdermal administration. Other methods of administration, e.g. by oral/enteral route, are possible under suitable conditions and with the correct formulations. The transfection complex may also be administered locally directly into a target tissue, such as an organ or a tumour. For application in vivo, the transfection complex should be presented in a pharmaceutically well tolerated form. For this purpose it may be combined with a pharmaceutically acceptable carrier. The formulation will depend on the method of administration. For injection or infusion the transfection complex may be present, for example, in isotonic saline solution or in an isotonic buffer such as PBS (phosphate buffered saline) or Ringer's solution, while for pulmonary administration it may take the form of a pharmaceutically acceptable aerosol, for example. Solid formulations may also be used, depending on the intended application, such as freeze-dried preparations which can be reconstituted with water before administration. The skilled man is familiar with suitable pharmaceutical carriers and formulations, e.g. from Gennaro (ed.), Remington: The Science and Practice of Pharmacy, 19th Ed., 1995, Mack Publishing Co., Easton, Pa., USA. In this way the transfection complex may be used as a pharmaceutical composition in gene therapy using a corresponding nucleic acid.

The dosage is chosen by the skilled man depending on the nature of the disease, the patient's condition, the therapeutic approach and other factors. Generally, for use in humans, the quantity of DNA administered will be in the range from 0.1 μg to 100 mg/kg of body weight, preferably 2.5 μg to 10 mg/kg of body weight.

One gene therapy application is the selective transfection of activated vascular endothelial cells which play an important role in inflammatory processes. By the introduction and expression of suitable genes in these cells the inflammatory response can be modulated (Harari et al., supra). A target-specific binding molecule which is suitable for this application is a monoclonal antibody against the cell surface antigen CD62E (E-selectin, ELAM-1), e.g. the monoclonal antibody which is produced by the hybridoma cell line H18/7 (ATCC HB-11684). A suitable nucleic acid would be, for example, an expression vector which is able to express the gene for the anti-inflammatory cytokine interleukine-10 (IL-10) (Henke et al., J Immunol 2000, 164(4):2131–41). For such an aopplication the transfection complex is preferably administered by intravenous injection.

Another clinical field of application is the gene therapy of cancers. Tumour cells can be selectively transfected by means of the present invention, by using target-specific binding molecules which bind selectively to specific surface antigens of tumour cells, e.g. antibodies against CD44v6, which is a marker for plate epithelial carcinomas (Heider et al., Cancer Immunol Immunother 1996, 43(4):245–53), or MART-1 (Ribas et al., Cancer Gene Ther 1999, 6:523–36), which is a marker protein for melanomas. Examples of suitable nucleic acids for such applications are expression vectors which are able to express the genes for the apoptosis initiating proteins E2F-1 (Dong et al., Cancer 1999, 86:2021–33) or apoptin (Pietersen et al., Gene Ther 1999, 6:882–92).

Procedures for the transfection of cells in vivo by the administration of nucleic acid/dendrimer complexes to animals are known from the prior art (Turunen et al., Gene Ther 1999, 6(1):6–11; Maruyama-Tabata et al., Gene Ther 2000, 7(1):53–60; Harada et al., Gene Ther 2000, 7(1):27–36). The choice of the manner of administration and the dosage depends on the nature of the disease, the patient's body weight, etc., and is within the capabilities of the skilled man.

The process according to the invention is particularly suitable for cells grown in cell culture in suspension (suspended cells), i.e. cells which are not attached to substrate surfaces as they grow. The process is particularly suitable for blood cells or blood cell lines, such as B- or T-cells or cell lines derived therefrom.

In another aspect the present invention relates to a composition containing a complex of nucleic acid and branched cationic polymer, in which the branched cationic polymer has the ability to form complexes with nucleic acids, characterised in that a proportion of the branched cationic polymer is biotinylated. Preferably, a cationic polymer of this kind is a dendrimer as described above.

In another aspect the present invention relates to a composition containing a complex of nucleic acid and dendrimer, characterised in that a proportion of the dendrimer molecules are biotinylated. Preferably, the proportion of dendrimer molecules which are biotinylated constitutes 0.01 to 100% (mol/mol), preferably 0.5 to 50% (mol/mol), more preferably 5 to 20% (mol/mol), most preferably 10 to 15% (mol/mol).

In another aspect the present invention relates to a composition containing a complex of nucleic acid and dendrimer, characterised in that a proportion of the dendrimer molecules are biotinylated, which may be prepared by mixing biotinylated dendrimer with non-biotinylated dendrimer in a ratio of 1:1 to 1:256 (wt/wt), preferably 1:2 to 1:128 (wt/wt), more preferably 1:4 to 1:24 (wt/wt), most preferably 1:6 to 1:10 (wt/wt).

In another aspect the present invention relates to a composition containing a complex of nucleic acid and dendrimer, wherein a proportion of the dendrimer molecules are biotinylated, which may be prepared by a process comprising the steps of:

(a) reacting dendrimer with an equimolar amount of an activated biotin or biotin derivative or a molar excess of activated biotin or activated biotin derivative, preferably a 2- to 64-fold molar excess, more preferably a 2- to 12-fold molar excess under conditions in which covalent bonding takes place between the dendrimer and the biotin or biotin derivative;

(b) mixing the biotinylated dendrimer formed in (a) with non-biotinylated dendrimer, preferably in a ratio by mass of 1:1 to 1:256, more preferably in a ratio by mass of from 1:4 to 1:24;

(c) incubating the mixture obtained in (b) with nucleic acid under conditions in which a complex of nucleic acid and dendrimer may be formed.

In another aspect, a composition of this kind contains a complex as defined in one of the preceding paragraphs, which additionally contains avidin or streptavidin and a biotinylated target-specific binding molecule. A target-specific binding molecule of this kind preferably binds specifically to a cell surface molecule, e.g. transferrin or an antibody.

In another aspect the invention relates to a reagent kit for introducing nucleic acid into cells, containing at least:

(a) dendrimer, wherein a proportion of the dendrimer molecules are biotinylated; and (b) avidin or streptavidin.

Such a kit contains the components in a common packaging unit, optionally with additional components and/or adjuvants, such as buffer solutions or the like and optionally with operating instructions and/or product information on paper, plastic film or an electronic data carrier. A reagent kit of this kind may advantageously be used for the process according to the invention. Preferably, a reagent kit of this kind contains, as additional component, at least one biotinylated target-specific binding molecule and/or at least one nucleic acid. In another aspect the present invention relates to the use of a reagent kit of this kind for introducing nucleic acid into cells, particularly suspended cells such as T- and B-cells.

In another aspect the present invention relates to a process for preparing a complex of nucleic acid and dendrimer, wherein a proportion of the dendrimer molecules are biotinylated, comprising the steps of:

(a) reacting dendrimer with an equimolar amount of an activated biotin or biotin derivative or a molar excess of activated biotin or biotin derivative, preferably a 2- to 64-fold molar excess, more preferably a 2- to 12-fold molar excess under conditions in which covalent bonding takes place between the dendrimer and the biotin or biotin derivative;

(b) mixing the biotinylated dendrimer formed in (a) with non-biotinylated dendrimer, preferably in a ratio by mass of 1:1 to 1:256, more preferably in a ratio by mass of from 1:4 to 1:24;

(c) incubating the mixture obtained in (b) with nucleic acid under conditions in which a complex of nucleic acid and dendrimer may be formed.

In another aspect the present invention relates to a composition containing dendrimer, wherein a proportion of the dendrimer molecules are biotinylated, which may be prepared by a process comprising the steps of:

(a) reacting dendrimer with an equimolar amount of activated biotin or biotin derivative or a molar excess of activated biotin or biotin derivative, preferably a 2- to 64-fold molar excess, more preferably a 2- to 12-fold molar excess under conditions in which covalent bonding takes place between the dendrimer and the biotin;

(b) mixing the biotinylated dendrimer formed in (a) with non-biotinylated dendrimer, preferably in a ratio by mass of 1:1 to 1:256, more preferably in a ratio by mass of from 1:4 to 1:24.

In another aspect the present invention relates to a pharmaceutical composition containing a dendrimer, wherein a proportion of the dendrimer molecules are biotinylated, as described hereinbefore, and optionally a pharmaceutically acceptable carrier.

In another aspect the present invention relates to a pharmaceutical composition containing a complex of nucleic acid and dendrimer, wherein a proportion of the dendrimer molecules are biotinylated, as described hereinbefore, and optionally a pharmaceutically acceptable carrier.

In another aspect the present invention relates to a pharmaceutical composition containing a complex of nucleic acid, dendrimer, avidin or streptavidin, and a target-specific binding molecule, wherein the target-specific binding molecule and a proportion of the dendrimer molecules are biotinylated, as described hereinbefore, and optionally a pharmaceutically acceptable carrier.

In another aspect the present invention relates to the use of a dendrimer, wherein a proportion of the dendrimer molecules are biotinylated, as described hereinbefore, in gene therapy.

In another aspect the present invention relates to the use of a complex of nucleic acid and dendrimer, wherein a proportion of the dendrimer molecules are biotinylated, as described hereinbefore, in gene therapy.

In another aspect the present invention relates to the use of a complex of nucleic acid, dendrimer, avidin or streptavidin, and a target-specific binding molecule, wherein the target-specific binding molecule and a proportion of the dendrimer molecules are biotinylated, as described hereinbefore, in gene therapy.

In another aspect the present invention relates to the use of a dendrimer, wherein a proportion of the dendrimer molecules are biotinylated, as described hereinbefore, for preparing a pharmaceutical composition for gene therapy.

In another aspect the present invention relates to the use of a complex of nucleic acid and dendrimer, wherein a proportion of the dendrimer molecules are biotinylated, as described hereinbefore, for preparing a pharmaceutical composition for gene therapy.

In another aspect the present invention relates to the use of a complex of nucleic acid, dendrimer, avidin or streptavidin, and a target-specific binding molecule, wherein the target-specific binding molecule and a proportion of the dendrimer molecules are biotinylated, as described hereinbefore, for preparing a pharmaceutical composition for gene therapy.

In another aspect the present invention relates to the use of a dendrimer, wherein a proportion of the dendrimer molecules are biotinylated, as described hereinbefore, in a process for introducing nucleic acid into cells in vivo, comprising the steps of:

(a) mixing a nucleic acid with a dendrimer, wherein a proportion of the dendrimer molecules are biotinylated, (b) mixing the resulting complex of nucleic acid and dendrimer with a second complex, consisting of avidin or streptavidin and a biotinylated target-specific binding molecule;

(c) administering the complex formed in step (b) to a plant or animal organism, optionally in conjunction with a pharmaceutically acceptable carrier.

EXAMPLES

Example 1

Figure 1:
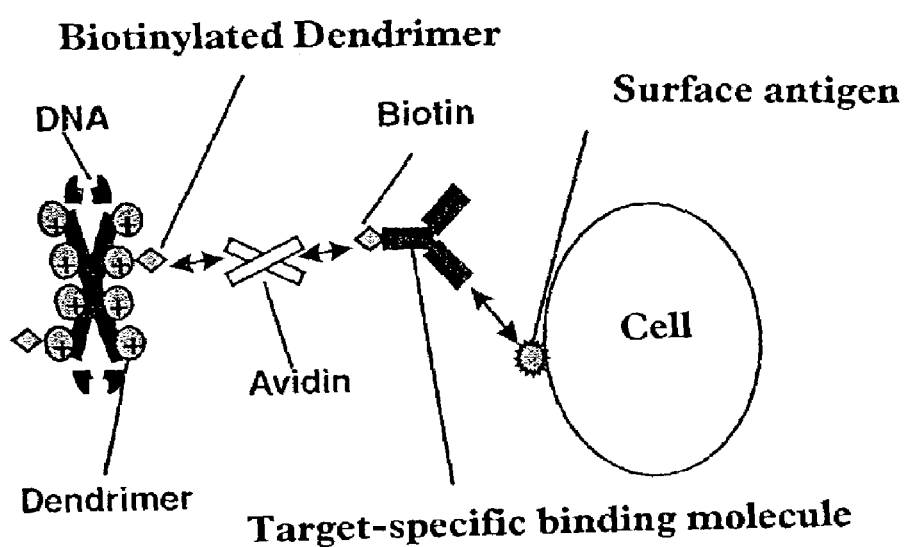
FIG. 1: Basic principle of the avidin-streptavidin system.

Targeted Transfection of K562 Cells with Biotinylated Transferrin/Different Stages of Biotinylation of the Transferrin Biotinylation Reactions Human holo-transferrin was obtained from Calbiochem (La Jolla, Calif., USA) and dissolved in PBS. The biotinylation was carried out with N-hydroxysuccinimide ester of D-biotinoyl-ϵ-aminocaproic acid (biotin-7-NHS) using a commercially obtainable Biotin Protein Labeling Kit (Roche Molecular Biochemicals, Hoffman-LaRoche AG, Grenzach-Wyhlen, Germany) in accordance with the manufacturer's instructions. The degree of biotinylation was measured using HABA (4'-hydroxyazobenzene-2-carboxylic acid) dye reaction (Fluka, Milwaukee, Wis., USA) and standard protein measurement (Hermanson, supra, pages 591–592).

The biotinylation of dendrimer (SuperFect®, Qiagen GmbH, Hilden, Germany), an activated 6th generation TAEA-PAMAM, was carried out with N-succinimidyl N-(+)-biotinyl-6-aminocaproate according to Hermanson, supra, pages 575–580. 4 mg of Superfect were reacted with the corresponding molar excess of biotin (4-, 8-, 16- or 32-fold). Dialysis was then carried out.

Cultivation of the Suspended Cells:

The cell line K562 (ATCC CCL-243) was first cultivated for three days in Spinner flasks in RPMI medium containing 10% FCS. The cell density at the start was $1.5 \times 10^5$ to $2 \times 10^5$ cells per ml. After three days the culture was diluted to a density of about $3 \times 10^5$ cells per ml. After another 24 hours' cultivation the cells were seeded in 96 well plates at the rate of 30,000 K562 cells per well in 100 µl. If there was another transfection the next day, the Spinner culture was diluted beforehand to a density of about $3 \times 10^5$ cells per ml.

Transfection:

1. For each five-fold mixture (which was subsequently used for four wells of a 96-well plate) 10 µl of a transferrin solution (diluted in medium without serum) was mixed with 10 µl of an avidin solution (Fluka, Milwaukee, Wis., USA; diluted in medium without serum) and the resulting mixture was incubated for 10 minutes at ambient temperature. It was calculated that 1 μg of avidin and 25 ng to 1 μg of biotinylated transferrin were used per well.

2. To form the complex, 150 μl of DNA (pCMVβ, Clontech Laboratories, Inc., Palo Alto, Calif., USA; an expression plasmid for β-galactosidase) solution was incubated with 100 μl of reagent solution (SuperFect reagent; mixture of biotinylated and non-biotinylated SuperFect in the ratio 1:8; the biotinylated SuperFect was prepared with a 4-fold molar excess of biotin reagent) for five minutes at ambient temperature. The amounts used corresponded to 0.5 μg of DNA and 1.5 μg of transfection reagent per well.

3. The complexes of (1) and (2) were mixed together and incubated for 30 minutes at ambient temperature.

4. 50 μl portions of the complexes from (3) were added to the cells in each well and mixed with the cell suspension and incubated for 48 hours.

5. Before the cells were lysed they were transferred into microtitre plates with conical bases. In these microtitre plates the cells can be pelleted by centrifuging for five minuites at 2000 rpm. Before being taken up in lysing buffer (5 mM $MgCl_2$, 1% NP-40, 100 mM NaCl, 10 mM Tris/HCl, pH 7.4) and returned to their original plates the cells and the original wells were washed twice with PBS.

6. Then, in order to determine the transfection efficiency, a β-galactosidase assay was carried out with ONPG (2-nitrophenyl-β-D-galactopyranoside, Merck KGaA, Darmstadt, Germany) as substrate or an X-Gal in situ staining was done (Ausubel et al. (Ed.), Current Protocols in Molecular Biology, Wiley & Sons, New York 1988, 9.5.12).

Figure 2:
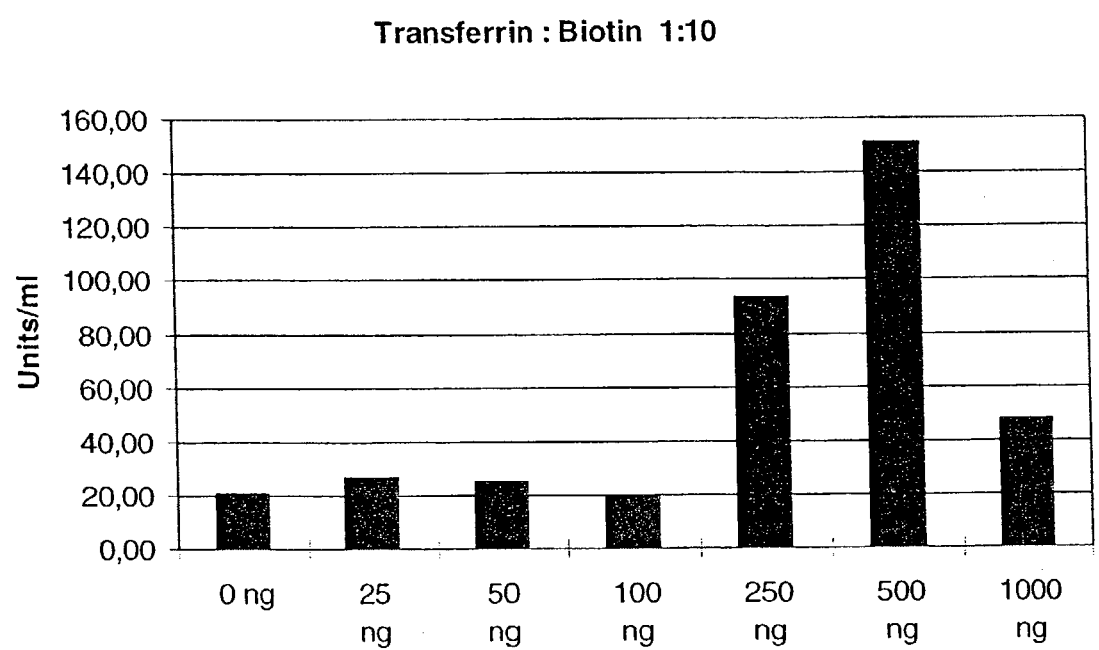
FIG. 2: Influence of the degree of biotinylation of the transferrin on the transfection efficiency. Biotinylation level 1:10 (transferrin/biotin). The values on the x axis indicate the quantity of biotinylated transferrin used per well in the transfection experiment. The values on the y axis indicate the β-galactosidase activity as a measure of the transfection efficiency. Cf. Example 1.
Figure 3:
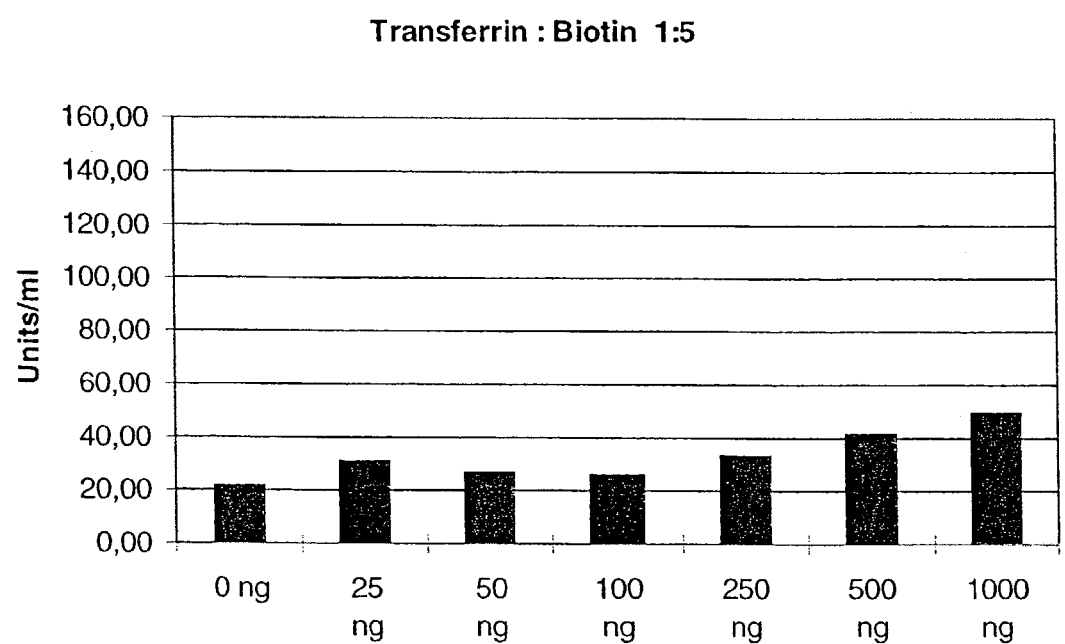
FIG. 3: Influence of the degree of biotinylation of the transferrin on the transfection efficiency. Biotinylation level 1:5 (transferrin/biotin). The values on the x axis indicate the quantity of biotinylated transferrin used per well in the transfection experiment. The values on the y axis indicate the β-galactosidase activity as a measure of the transfection efficiency. Cf. Example 1.
Figure 4:
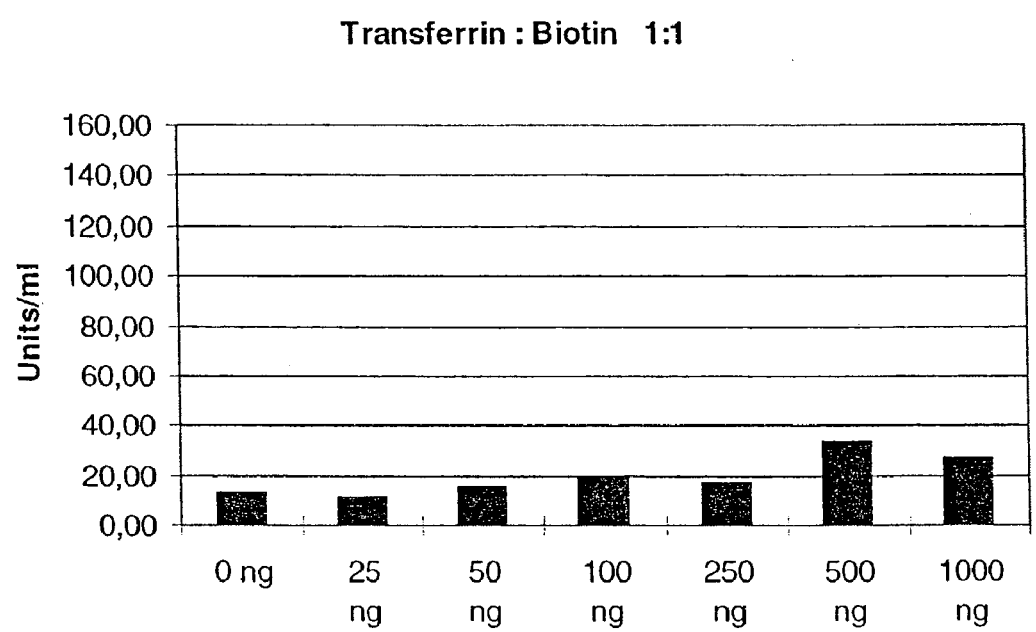
FIG. 4: Influence of the degree of biotinylation of the transferrin on the transfection efficiency. Biotinylation level 1:1 (transferrin/biotin). The values on the x axis indicate the quantity of biotinylated transferrin used per well in the transfection experiment. The values on the y axis indicate the β-galactosidase activity as a measure of the transfection efficiency. Cf. Example 1.

In accordance with the procedure for the targeted transfection of suspended cells, K562 cells were transfected on the 96 well scale. Transferrins were used for which biotinylation levels of on average 10, 5 or one biotin molecule per transferrin molecule had been measured. With a biotinylation level of on average 10 biotins per transferrin molecule, when a quantity of 250 ng to 1000 ng of transferrin is used per well, there is an increase in the transfection efficiency of about a factor of 7.5. For biotinylation levels of 1:5 and 1:1 there was only a slight increase, not more than two-fold (cf. FIGS. 2 to 4). A higher biotinylation level (1:13) showed a smaller effect on transfection efficiency. In another experiment, the percentage of transfected cells for 1:10 biotinylated transferrin was determined by X-Gal in situ staining. Whereas the β-galactosidase activity could be increased from 12.2 units/ml (without transferrin) to 71.7 units/ml (500 ng of biotinylated transferrin), a transfection efficiency of 28% transfected cells was determined for 500 ng of biotinylated transferrin.

The effect of the biotinylation level of the SuperFect on the transfection was also investigated. Biotinylated SuperFect in which a four-, eight-, 16- or 32-fold excess of biotin had been used in the biotinylation reaction (hereinafter referred to as 1:4, 1:8, 1:16 and 1:32 biotinylated) was used. 0.5 μg of DNA (pCMVβ; an expression plasmid for β-galactosidase) and 1.5 μg of SuperFect reagent were used per well for the transfection. Between half (½) ad ¹⁄₁₂₈ of biotinylated SuperFect was added. As the quantity of biotinylated SuperFect increases the transfection efficiency falls.

In addition, for all four differently biotinylated SuperFect mixtures, experiments were conducted in which increasing amounts of avidin were added to the SuperFect-biotinylated SuperFect/DNA complexes. Between 10 ng and 5000 ng of avidin were used per well (of a 96 well plate) in a volume of 10 μl per five-fold mixture. The incubation with avidine lasted for 30 minutes at ambient temperature. As the amount of avidin increases there is initially an increase in the transfection efficiency, which can be measured as β-galactosidase activity. With a proportion of ⅛-biotinylated SuperFect there was a reduction in the β-galactosidase activity over 1000 ng of avidin per well. For further experiments, 1:4 biotinylated SuperFect was used in ⅛ mixtures and 1000 ng of avidin per well. The use of biotinylated SuperFect in conjunction with avidin and biotinylated transferrin (ratio of 10 molecules of biotin to 1 molecule of transferrin) makes it possible to increase the transfection efficiency in K562 cells from 2–5% to more than 25% transfected cells.

Example 2

Figure 5:
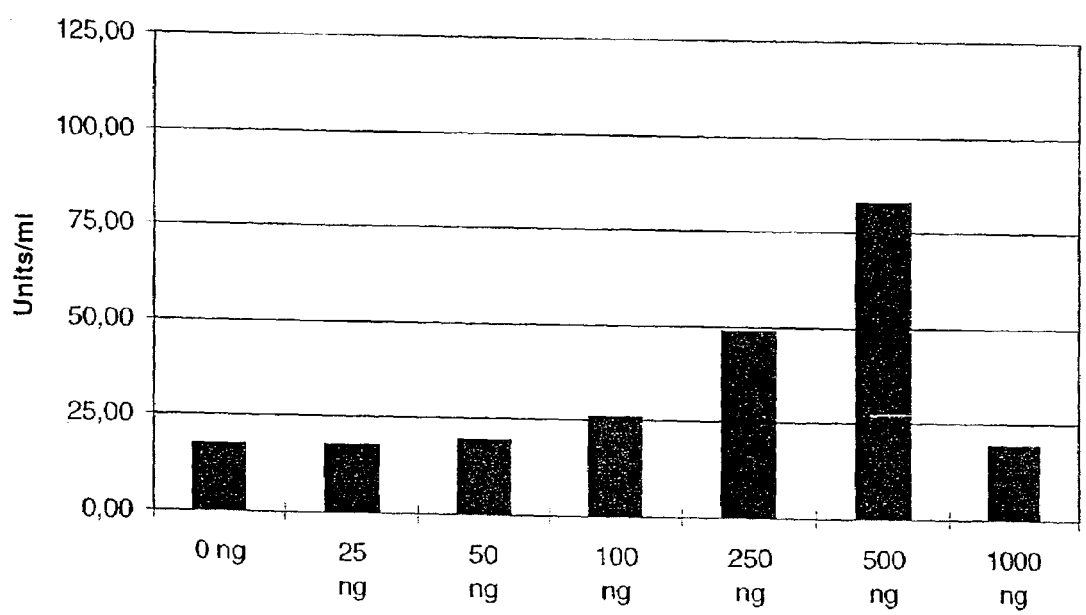
FIG. 5: Transfection efficiency for a different sequence of complex formation. Process steps: (a) avidin+biotinylated transferrin; 10 minutes' incubation; (b) SuperFect (SF)/biotinylated SF+DNA; 5 minutes' incubation; (c) mixing the two complexes; 20 minutes' incubation. The values on the x axis indicate the quantity of transferrin used per well in the transfection experiment. The values on the y axis indicate the β-galactosidase activity as a measure of the transfection efficiency. Cf. Example 2.
Figure 6:
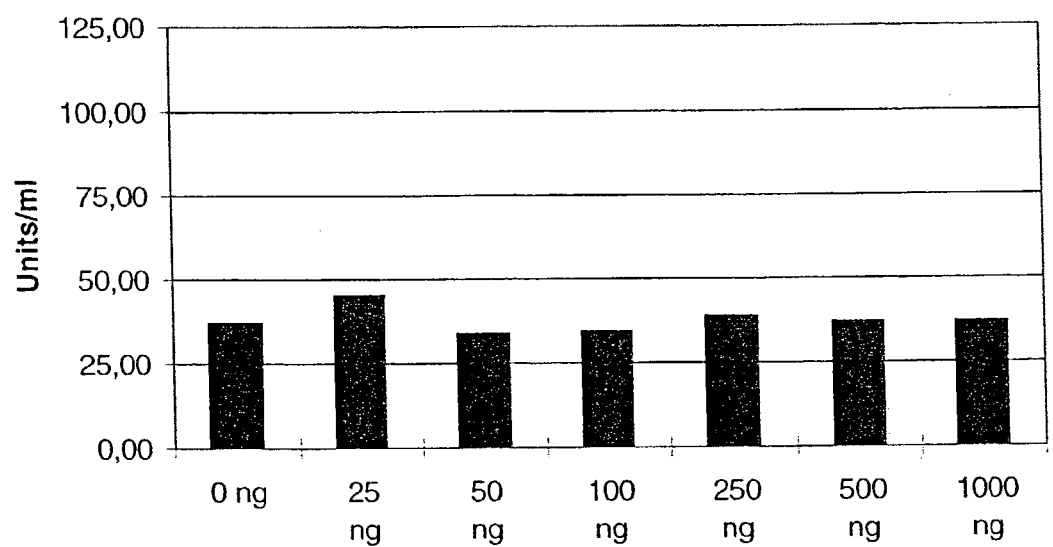
FIG. 6: Transfection efficiency for a different sequence of complex formation. Process steps: (a) (SF)/biotinylated SF+DNA; 5 minutes' incubation; (b) addition of avidin; 10 minutes' incubation; (c) addition of biotinylated transferrin; 20 minutes' incubation. The values on the x axis indicate the quantity of transferrin used per well in the transfection experiment. The values on the y axis indicate the β-galactosidase activity as a measure of the transfection efficiency. Cf. Example 2.
Figure 7:
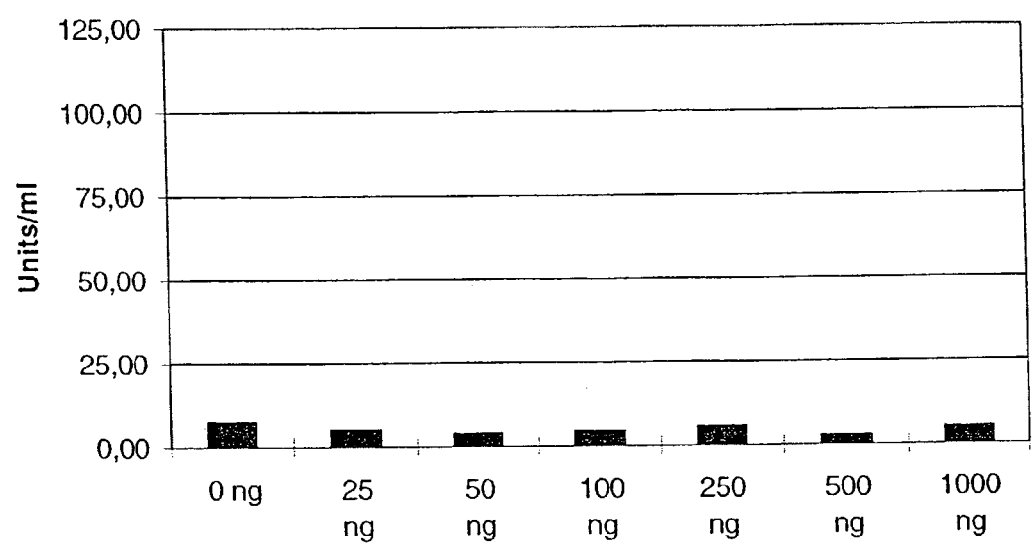
FIG. 7: Transfection efficiency for a different sequence of complex formation. Process steps: (a) biotinylated SF+avidin; 10 minutes' incubation; (b) addition of SuperFect; mixing; (c) addition of DNA; 5 minutes' incubation; (d) addition of biotinylated transferrin; 30 minutes' incubation. The values on the x axis indicate the quantity of transferrin used per well in the transfection experiment. The values on the y axis indicate the β-galactosidase activity as a measure of the transfection efficiency. Cf. Example 2.

Transfection Efficiency as a Function of the Sequence of the Process Steps in the Formation of the Transfection Complex In order to establish whether the order in which the individual components are added to the complexes has an influence on the increase in transfection efficiency, transfection experiments were carried out on K562 cells, keeping to the following sequences:

a) 1. Avidin+biotinylated transferrin; 10 minutes' incubation
   2. SuperFect (SF)/biotinylated SF+DNA; 5 minutes' incubation
   3. mixing the two complexes; 20 minutes' incubation b) 1. (SF)/biotinylated SF+DNA; 5 minutes' incubation
   2. addition of avidin; 10 minutes' incubation
   3. addition of biotinylated transferrin; 20 minutes' incubation c) 1. biotinylated SF+avidin; 10 minutes' incubation
   2. addition of SuperFect; mixing
   3. addition of DNA; 5 minutes' incubation
   4. addition of biotinylated transferrin; 30 minutes' incubation The transfection efficiency for these three variants is shown in FIGS. 5, 6 and 7.

The effect of increasing the transfection efficiency by the biotin-avidin system only occurs if DNA and SuperFect/biotinylated SuperFect and avidin and biotinylated transferrin are complexed separately from one another and the two complexes are only mixed together later. If the biotinylated SuperFect is pre-incubated with the avidin there is even a massive loss of transfection efficiency, as presumably the formation of the SuperFect/DNA complex is impeded.

Example 3

Direct Coupling of Avidin to SuperFect

As an alternative to a system in which biotinylated SuperFect, avidin and biotinylated transferrin are used, a system was tested in K562 cells which is based on a direct chemical coupling of avidin to SuperFect. The coupling was carried out according to Hermanson, supra, pages 575–583.

Figure 8:
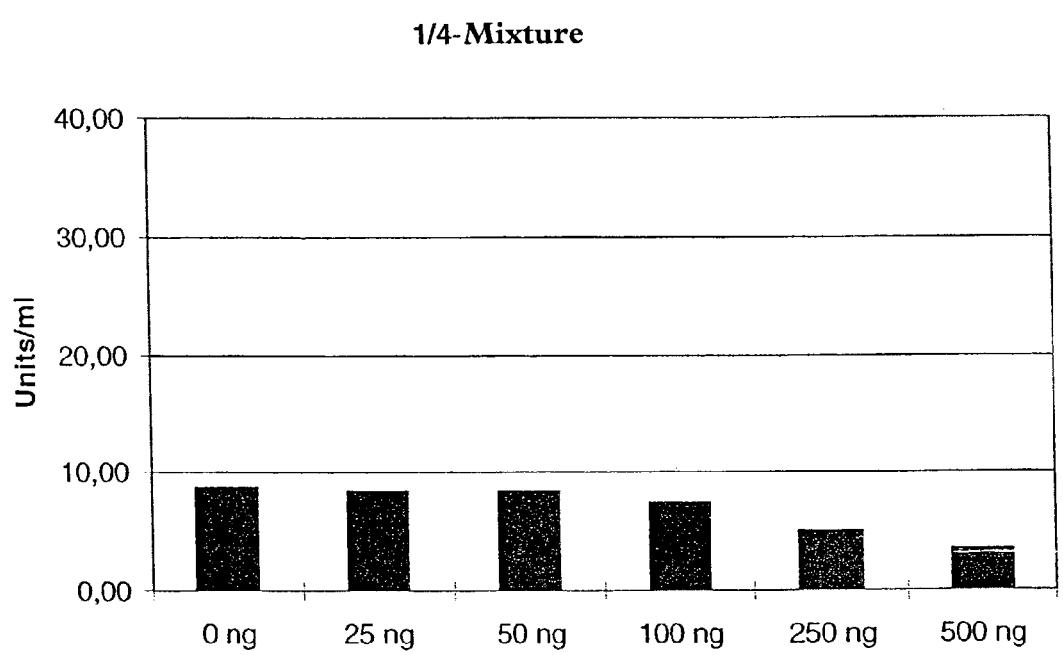
FIG. 8: Transfection efficiency when avidin is coupled directly to SuperFect. ¼ addition of avidin-SF coupling product to the total quantity of SuperFect. The values on the x axis indicate the quantity of biotinylated transferrin used per well in the transfection experiment. The values on the y axis indicate the β-galactosidase activity as a measure of the transfection efficiency. Cf. Example 3.
Figure 9:
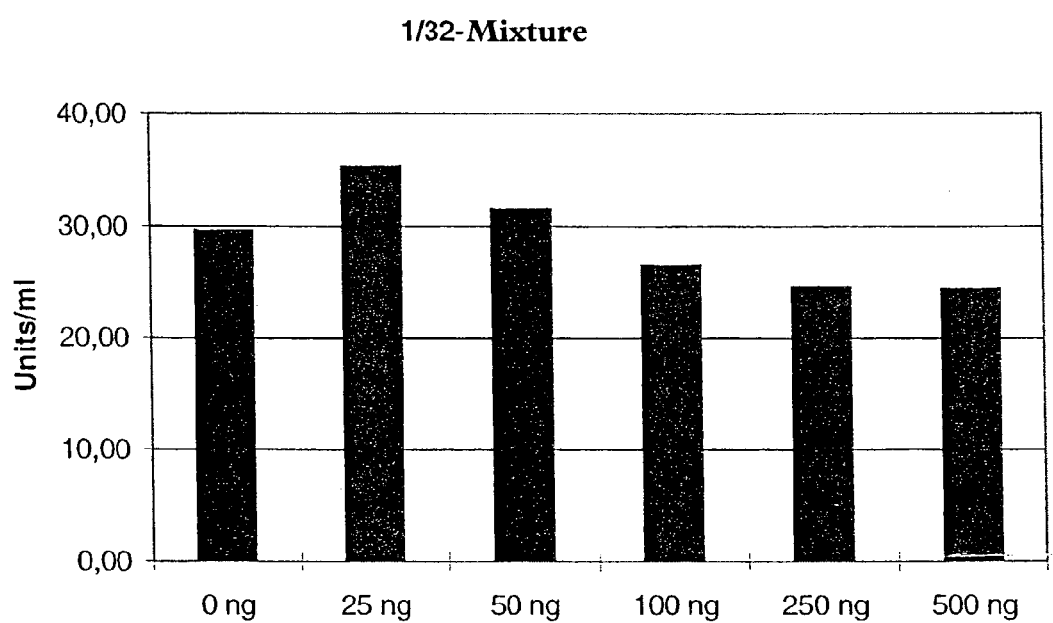
FIG. 9: Transfection efficiency when avidin is coupled directly to SuperFect. 1/32 addition of avidin-SF coupling product to the total quantity of SuperFect. The values on the x axis indicate the quantity of biotinylated transferrin used per well in the transfection experiment. The values on the y axis indicate the β-galactosidase activity as a measure of the transfection efficiency. Cf. Example 3.
Figure 10:
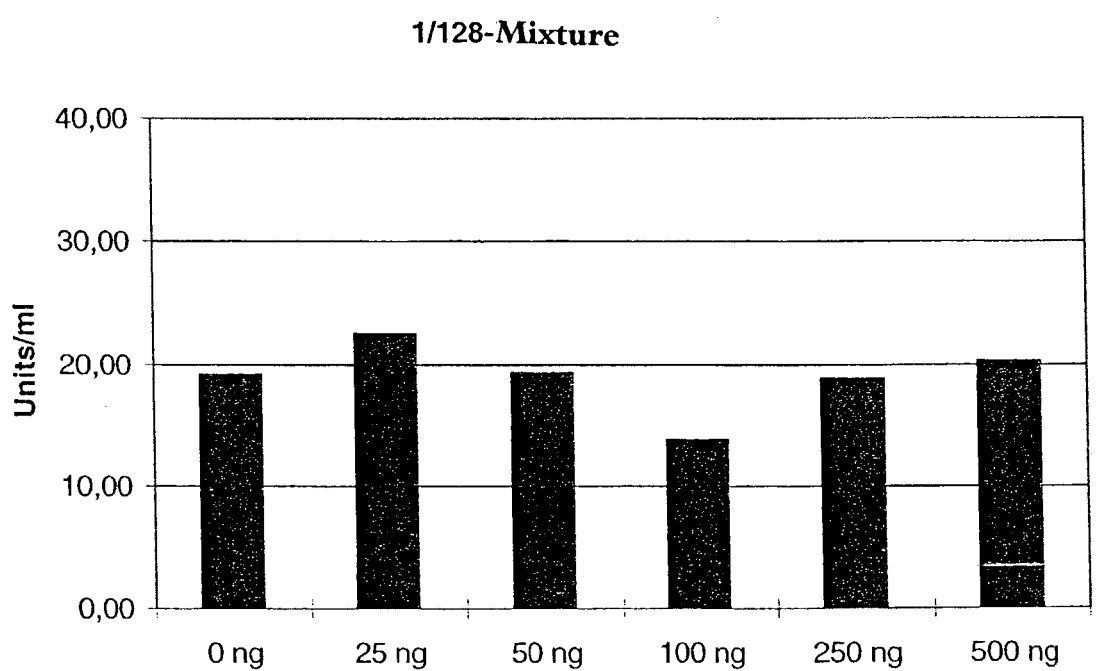
FIG. 10: Transfection efficiency when avidin is coupled directly to SuperFect. 1/128 addition of avidin-SF coupling product to the total quantity of SuperFect. The values on the x axis indicate the quantity of biotinylated transferrin used per well in the transfection experiment. The values on the y axis indicate the β-galactosidase activity as a measure of the transfection efficiency. Cf. Example 3.

Avidin/SuperFect coupling products in which coupling had been carried out for 2 or 24 hours or in which a bidirectional linker (N-succinimidyl-3-(2-pyridyldithio)-propionate) had been used were investigated. FIGS. 8, 9 and 10 show, by way of example, the results for an avidin/SuperFect coupling product of two hours with the incubation steps carried out as follows:

1. 10 μl of a SuperFect/avidin coupling product solution+10 μl of a solution containing biotinylated transferrin (1:10 biotinylated; the concentrations were selected so as to achieve the desired final ratio (1:4, 1:32, 1:128 (wt/wt)

transferrin/coupling product) and a final concentration of 1.5 μg of SuperFect per well); 15 minutes' incubation at ambient temperature;
2. Addition of 90 μl of SuperFect dilution; 10 minutes' incubation at ambient temperature;
3. Addition of 150 μl of DNA solution (pCMVβ); 10 minutes' incubation at ambient temperature.

All the dilutions were prepared in medium without serum; 0.5 μg of DNA, 1.5 μg of SuperFect reagent with varying amounts of avidin-SF coupling product (see Figures) were used per well of a 96 well plate.

The x axis shows the quantities of biotinylated transferrin used per well and the titles of the diagrams give the proportion of avidin-SF coupling product in the total quantity of SuperFect. The results for a conventional SuperFect transfection carried out in parallel were 10.3 units/ml.

Depending on the quantity of avidin-SuperFect coupling product used, there is an increase in the transfection efficiency ($\frac{1}{32}$ and $\frac{1}{128}$ mixture). However, there are no instances in which a further increase in efficiency is brought about by biotinylated transferrin. This result was also obtained when the sequence of incubations was altered (1. mixing SF with avidin-SF coupling product; 2. adding the DNA; 3. adding the biotinylated transferrin) and when alternative coupling products were used (coupling over 24 hours; use of a bidirectional linker).

Example 4

Targeted Transfection of Jurkat Cells with Biotinylated Anti-CD3 Antibody

Antibody

THe antibody used was the commercially obtainable biotinylated αhumanCD3 from Sigma (Sigma-Aldrich Chemie GmbH, Deisenhofen, Germany).

Cultivation of the Suspended Cells

The cell line Jurkat (DSMZ ACC 282) was first cultivated for three days in Spinner flasks in RPMI medium with 10% FCS. The cell density to start with was $1.5 \times 10^5$ to $2 \times 10^5$ cells per ml. After three days the culture was diluted to a density of about $3 \times 10^5$ cells per ml. After another 24 hours cultivation the cells were seeded in 96 well plates at the rate of 50,000 cells per well in 100 μl. If there was another transfection the next day, the Spinner culture was diluted beforehand to a density of about $3 \times 10^5$ cells per ml.

Transfection:
1. For each five-fold mixture (which was subsequently used for four wells of a 96-well plate) 10 μl of an antibody solution (diluted in medium without serum) was mixed with 10 μl of an avidin solution (diluted in medium without serum) and incubated for 10 minutes at ambient temperature. It was calculated that 0.75 μg of avidin and 25 ng to 1 μg of biotinylated antibody were used per well.
2. To form the complex, 150 μl of DNA (pCMVβ, an expression plasmid for β-galactosidase) solution was incubated with 100 μl of reagent solution (SuperFect reagent; mixture of biotinylated and non-biotinylated SuperFect in a ratio 1:8; the biotinylated SuperFect was prepared with a 4-fold molar excess of biotin reagent) for five minutes at ambient temperature. The amounts used corresponded to 0.5 μg of DNA and 1.5 μg of transfection reagent per well.
3. The complexes of (1) and (2) were mixed together and incubated for 30 minutes at ambient temperature.
4. 50 μl portions of the complexes from (3) were added to the cells in each well and mixed with the cell suspension and incubated for 48 hours.
5. Before the cells were lysed they were transferred into microtitre plates with conical bases. In these microtitre plates the cells can be pelleted by centrifuging for five minutes at 2000 rpm. Before being taken up in lysing buffer and returned to their original plates the cells and the original wells were washed twice with PBS.
6. Then, in order to determine the transfection efficiency, a β-galactosidase assay was carried out with ONPG as substrate or an X-Gal in situ staining was done.

Figure 11:
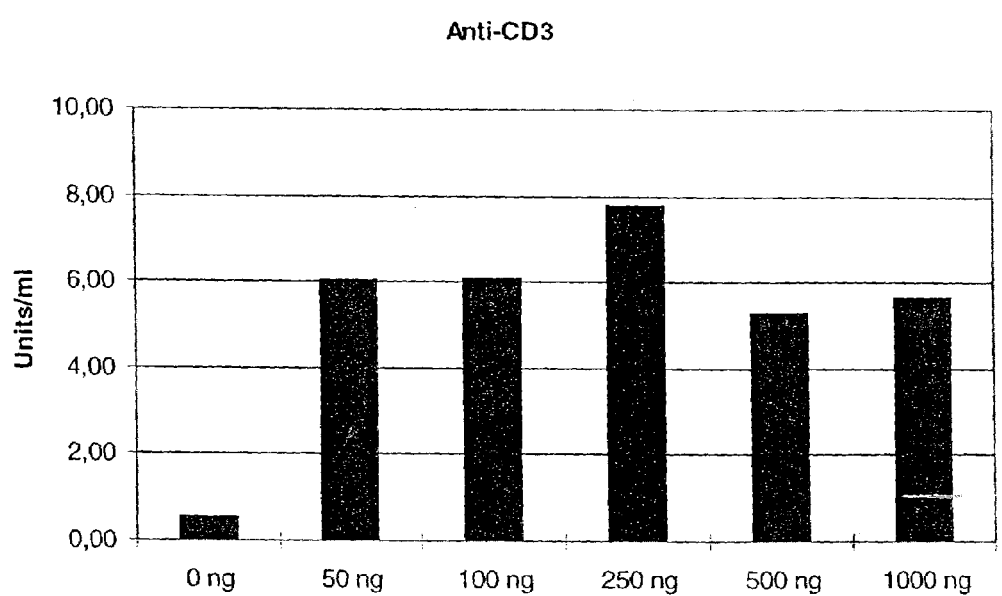
FIG. 11: Transfection efficiency of the transfection of Jurkat cells with biotinylated anti-CD3 antibodies. The values on the x axis indicate the quantity of biotinylated antibody used in the transfection experiment. The values on the y axis indicate the β-galactosidase activity as a measure of the transfection efficiency. Cf. Example 4.

In the experiment described here, the Jurkat T-cell line was transfected with biotinylated antiDC3 antibody. After the system had been optimised 0.75 μg of avidin per well and 1:4 biotinylated SuperFect were used in a $\frac{1}{9}$ mixture. The quantity of biotinylated antibody is shown under the bars in the diagram in FIG. 11. The value for control transfection with SuperFect (without avidin, biotinylated SuiperFect) was 0.9 units/ml.

For 250 ng and 500 ng of antibody the percentage of transfected cells was determined by X-Gal staining; it was 4.8% (250 ng) and 5.0% (500 ng) of the cells. This result was confirmed by further experiments.

The invention claimed is:

1. A composition for the transfection of cells comprising a complex of nucleic acid and dendrimer, wherein a proportion of the dendrimer is biotinylated and a portion of the dendrimer molecules is not biotinylated, wherein the portion of the dendrimer molecules that are biotinylated is 0.5 to 50% (mol/mol) of the total amount of dendrimer molecules.

2. The composition according to claim 1, wherein said proportion of dendrimer molecules that are biotinylated in the total quantity of dendrimer molecules is 5 to 20% (mol/mol).

3. The composition according to claim 1, wherein said complex further comprises avidin or streptavidin and a biotinylated target-specific binding molecule.

4. The composition according to claim 3, wherein said target-specific binding molecule binds to a cell surface molecule.

5. The composition according to claim 3, wherein said target-specific binding molecule is transferrin or an antibody.

6. A composition of dendrimer, wherein a portion of said dendrimer molecules are biotinylated, said composition prepared by a process comprising the steps:
   (a) reacting dendrimer with an equimolar amount of activated biotin or activated biotin derivative or a molar excess of activated biotin or activated biotin derivative, in a 2- to 64-fold molar excess under conditions in which covalent bonding takes place between said dendrimer and said activated biotin or activated biotin derivative; and
   (b) mixing the biotinylated dendrimer formed in (a) with non-biotinylated dendrimer, in a ratio by mass of 1:1 to 1:256.

7. A pharmaceutical composition comprising a composition according to claim 1 or claim 6 and a pharmaceutically acceptable carrier.

8. The composition of claim 6, wherein said molar excess of said activated biotin or said activated biotin derivative is a 2- to 12-fold molar excess.

9. The composition of claim 6, wherein said ratio by mass of said biotinylated dendrimer to said non-biotinylated dendrimer is 1:4 to 1:24.

10. A method of introducing nucleic acid into cells in vitro or in vivo, comprising the steps of:
  (a) mixing a nucleic acid with a dendrimer, wherein a proportion of said dendrimer molecules are biotinylated, wherein the fraction of the dendrimer molecules that are biotinylated is 5 to 20% (mol/mol) of the total amount of dendrimer molecules;
  (b) mixing the resulting complex of nucleic acid and dendrimer with a second complex comprising avidin or streptavidin and a biotinylated target-specific binding molecule; and
  (c) incubating the complex formed in step (b) with cells.

11. The method according to claim 10, wherein the cells grow in a suspension culture.

12. The method according to one of claims 10 or 11, wherein said cells are blood cells or blood cell lines.

13. The method according to claim 12, wherein the cells are B- or T-cells or cell lines derived therefrom.

14. A reagent kit for introducing nucleic acid into cells, said kit comprising:
  (a) dendrimer, wherein a proportion of said dendrimer molecules are biotinylated and a fraction of the dendrimer cells is not biotinylated; and
  (b) avidin or streptavidin.

15. The reagent kit according to claim 14, further comprising a biotinylated target-specific binding molecule and/or a nucleic acid.

16. A process of preparing a composition comprising a complex of nucleic acid and branched cationic polymer, wherein the branched catiomc polymer forms complexes with nucleic acids, and wherein a proportion of the branched cationic polymer is biotinylated, said process comprising the steps of:
  (a) reacting dendrimer with an equimolar amount of activated biotin or an activated biotin derivative or a molar excess of activated biotin or activated biotin derivative, in a 2- to 64-fold molar excess under conditions in which covalent bonding takes place between said dendrimer and said activated biotin or activated biotin derivative;
  (b) mixing the biotinylated dendrimer formed in (a) with non-biotinylated dendrimer in a ratiobymass of 1:1 to 1:256; and
  (c) incubating the mixture obtained in (b) with nucleic acid under conditions in which a complex of nucleic acid and dendrimer is formed.

17. The process of claim 16, wherein said molar excess of said activated biotin or said activated biotin derivative is a 2- to 12-fold molar excess.

18. The process of claim 16, wherein said ratio by mass of said biotinylated dendrimer to said non-biotinylated dendrimer is 1:4 to 1:24.

19. A method of preparing a complex of nucleic acid and dendrimer, wherein a proportion of said dendrimer molecules are biotmylated, said method comprising the steps of:
  (a) reacting dendrimer with an equimolar amount of activated biotin or an activated biotin derivative or a molar excess of activated biotin or activated biotin derivative, in a 2- to 64-fold molar excess under conditions in which covalent bonding takes place between said dendrimer and said activated biotin or activated biotin derivative;
  (b) mixing the biotinylated dendrimer formed in (a) with non-biotinylated dendrimer in a ratio by mass of 1:1 to 1:256; and
  (c) incubating the mixture obtained in (b) with nucleic acid under conditions in which a complex of nucleic acid and dendrimer is formed.

20. The method of claim 19, wherein said molar excess of said activated biotin or said activated biotin derivative is a 2- to 12-fold molar excess.

21. The method of claim 19, wherein said ratio by mass of said biotinylated dendrimer to said non-biotinylated dendrimer is 1:4 to 1:24.

22. A method for preparing a dendrimer, wherein a proportion of the dendrimer molecules are biotinylated, said method comprising the steps of:
  (a) reacting dendrimer with an equimolar amount of activated biotin or activated biotin derivative or a molar excess of activated biotin or activated biotin derivative, in a 2- to 64-fold molar excess under conditions in which covalent bonding takes place between said dendrimer and said activated biotin or activated biotin derivative; and
  (b) mixing the biotinylated dendrimer formed in (a) with non-biotinylated dendrimer, in a ratio by mass of 1:1 to 1:256.

23. The method of claim 22, wherein said molar excess of said activated biotin or said activated biotin derivative is a 2- to 12-fold molar excess.

24. The method of claim 22, wherein said ratio by mass of said biotinylated dendrimer to said non-biotinylated dendrimer is 1:4 to 1:24.

25. A method of introducing nucleic acid into cells in vivo, said method comprising the steps of:
  (a) mixing a nucleic acid with a dendrimer, wherein a proportion of said dendrimer molecules are biotinylated wherein the fraction of the dendrimer molecules that are biotinylated is 5 to 20% (mol/mol) of the total amount of dendrimer molecules,
  (b) mixing the resulting complex of nucleic acid and dendrimer with a second complex, comprising avidin or streptavidin and a biotinylated target-specific binding molecule; and
  (c) administering the complex formed in step (b) to a plant or animal organism, optionally in conjunction with a pharmaceutically acceptable camer.

* * * * *